United States Patent [19]
Watts, Jr. et al.

[11] 3,984,487
[45] Oct. 5, 1976

[54] PREPARATION OF PETACHLORONITROBENZENE

[75] Inventors: Lewis W. Watts, Jr.; Ernest L. Yeakey, both of Austin, Tex.

[73] Assignee: Texaco Development Corporation, Houston, Tex.

[22] Filed: Dec. 8, 1975

[21] Appl. No.: 638,394

[52] U.S. Cl. .............................................. 260/646
[51] Int. Cl.² ............................................ C07C 79/12
[58] Field of Search ................................... 260/646

[56] References Cited
FOREIGN PATENTS OR APPLICATIONS
620,338   5/1961   Canada ........................... 260/646
1,004,407  9/1965   United Kingdom ................ 260/646

Primary Examiner—Leland A. Sebastian
Attorney, Agent, or Firm—Carl G. Ries; Thomas H. Whaley; Lee G. Meyer

[57] ABSTRACT

A novel method for preparing pentachloronitrobenzene directly from the corresponding pentachlorobenzonitrile compound is disclosed. Pentachlorobenzonitrile is heated in the presence of an excess of sulfuric acid and a nitrating agent, e.g., nitric acid at elevated temperatures of from about 100°C to about 160°C for a time sufficient to convert the pentachlorobenzonitrile to a pentachloronitrobenzene.

In one embodiment the pentachlorobenzonitrile compound is first heated in the presence of an excess of concentrated sulfuric acid at temperatures in excess of 180°C to activate the pentachlorobenzonitrile and the activated material is then heated at lower temperatures of about 100° to 120°C in the presence of a nitrating agent to convert the activated pentachlorobenzonitrile to the corresponding pentachloronitrobenzene.

4 Claims, No Drawings

PREPARATION OF PETACHLORONITROBENZENE

BACKGROUND OF THE INVENTION

1. Field of the Invention

This invention relates to an improved process for preparing polychloronitrobenzene and more particularly to a process for synthesizing pentachloronitrobenzene directly from the corresponding pentachlorobenzonitrile compound.

2. Prior Art

Pentachloronitrobenzene is a well known fungicide as shown in *Analytical Methods for Pesticides, Plant Growth Regulators, and Food Additives*, Zweig, C., Ed., Vol. III, 127, Academic Press, N.Y. (1964). Heretofore, producing pentachloronitrobenzene required the use of the trichlorobenzene with a nitrating agent and excess chlorine in the presence of a strong chloro acid such as chlorosurfonic acid. Other methods of producing this compound include chlorinating nitrobenzene in the presence of a strong acid and iodine and nitrating pentachlorobenzene.

The prior art methods require the chlorination of the previously nitrated compound and/or the simultaneous nitration and/or chlorination of a partially substituted compound wherein the nitration occurs at a previously unsubstituted site. These prior art methods are somewhat costly. For example, the direct nitration of pentachlorobenzene is particularly disadvantageous owing to the difficulty and expense encountered in preparing the pentachlorobenzene starting material.

It has now been found that pentachlorobenzonitrile can be selectively converted to the corresponding pentachloronitrobenzene in accordance with the instant invention. This is surprising in that it is known that an acid anilide, such as acetanilide, (Ar-NHCOR), will not undergo hydrolysis and subsequent oxidation to the corresponding nitro compound. In this process the Ar-N bond is not broken but the ring is nitrated at the para position, Morrison and Boyd, *Organic Chemistry* 1962, p. 559. Additionally it is known that halogenated aromatics undergo nitration in the presence of nitric acid and a strong protonic acid by substitution of a halide group, Chemical Reviews Vol. 40, 1947. Therefore, reactions of the instant type led to polynitrated compounds formed by replacement of more than one chloro atom. Thus, it was particularly surprising when it was discovered that a fully substituted pentachlorobenzonitrile molecule containing Ar-CN bonding could be selectively converted to pentachloronitrobenzene. Such a process is particularly advantageous owing to the fact that an economical process for producing commercial amounts of pentahalobenzonitrile has recently been developed.

SUMMARY OF THE INVENTION

In accordance with the broad aspects of the instant invention, a pentachloronitrobenzene of the formula:

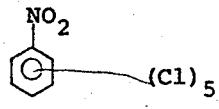

can be synthesized in good yields by heating the corresponding pentachlorobenzonitrile of the formula:

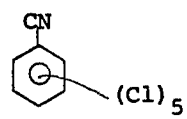

with an excess of a strong protonic acid at elevated temperatures of from about 100° to 160° in the presence of an effective amount of nitrating agent, e.g., nitric acid. The inventive method provides a resultant pentachloronitrobenzene of high purity.

DESCRIPTION OF THE PREFERRED EMBODIMENTS

Although it is preferable to accomplish the nitration in accordance with the instant invention in a single step, it is possible to carry out the process in two steps. When the process is carried out in a single step the pentachlorobenzonitrile, the strong protonic acid and the nitrating agent are heated to temperatures of from 130° to 160°C for a time sufficient to effect the desired nitration reaction. In the two step process the pentachlorobenzonitrile and the strong protonic acid are initially heated in a first step to temperatures in excess of 180°C and preferably in excess of 200°C to activate the pentachlorobenzonitrile. In a second step the nitrating agent is added to the crude reaction product of the first step and the admixture heated at relatively lower temperatures of from 100° to 130°C.

The two step process may be convenient in situations wherein concentrated nitric acid is used as the nitrating agent. Performing the nitration in a single step requires the use of higher nitration temperatures to achieve desirable reaction rates. The reason for this phenomena is not readily understood, but because under certain processing conditions it may be undesirable to heat a nitric acid/strong protonic acid mixture to temperatures in excess of about 130°C, the two step method provides an alternative.

In accordance with the invention, the strong protonic acid used may be any of the commercially known mineral acids that are non-deleterious to the reaction. The following is given by way of explanation and not meant to be limiting. It is believed that the strong acid is required to, in some manner, activate the pentachlorobenzonitrile for subsequent selective nitration. This activation is believed to take place whether the instant invention is practiced in a single step or in two steps. The reason for the higher temperature requirements to activate the starting material in the two step process is not completely understood.

The preferred strong protonic acid is sulfuric acid. The acid concentration must be sufficient to activate the pentachlorobenzonitrile. The concentration will depend upon the acid and the nitrating agent, but can be readily determined by the skilled artisan. When sulfuric acid is utilized, concentrations below 50% $H_2SO_4$ by total weight have not been found effective in activating the pentachlorobenzonitrile compound. Concentrations above about 75% $H_2SO_4$ by total weight have been found particularly effective in accordance with the inventive process. The amount of the strong acid used does not appear critical; and will, of course, depend on the concentration and the acid. Preferably, an excess of acid is utilized in concentrations and/or amounts sufficient to provide a molar excess of the strong acid in the reaction mixture.

The nitrating agent may be any of the well known agents used for nitrating reactions generally. Useful agents provide the nitryl ($NO_2$) specie under the reaction condition and are relatively weaker acids than the strong acid utilized. Examples of suitable agents are nitric acid, nitric acid anhydride, organic nitrates, alkali nitrates and nitrogen tetroxides. The preferred nitrating agent is nitric acid with concentrated nitric acid or fuming nitric being most preferred. Generally, the amount of nitrating agent used is a stoichiometric amount based on the pentachlorobenzonitrile compound. When the two step process is utilized, an excess of the agent is preferred. In carrying out the reaction in a single step, a large molar excess of the strong protonic acid is initially present. The nitric acid nitrating agent is then added incrementally until a stoichiometric amount of nitric acid with respect to the pentachlorobenzonitrile has been added. Additional nitric acid is then added as required to obtain an access of the nitrating agent.

In carrying out the process of the instant invention, temperatures in the range of from about 100° to about 160°C are effective in nitration of the pentachlorobenzonitrile to the corresponding nitrobenzene compound. The pressures utilized are generally those required to keep the reactants and products substantially in liquid phase. In practicing the instant invention in a single step, it has been found that generally higher temperatures e.g., 130° to 160°C are required in order to obtain desirable nitration rates. When the instant process is carried out in two steps, relatively higher temperatures are used to initially activate the pentachlorobenzonitrile in the presence of the strong acid alone. The nitration of the activated material can then be accomplished at relatively lower temperatures e.g., 100°C in the presence of the added nitrating agent.

Generally, temperatures in excess of 180°C are required to activate the pentachlorobenzonitrile in the two step process, but the actual temperature will depend on the strong protonic acid used, the concentration of the acid and the amount used. Temperatures in the range of 200° to 220°C are preferred for the activation step. Nitration is then accomplished in the second step at temperatures in the range of 100°C to about 130°C. In accordance with the single step method, i.e., when the pentachlorobenzonitrile is not first activated, in a separate step, higher temperatures in the range of about 130° to 160°C are required to obtain the desired rate of nitration.

When practicing the instant process in two steps, it has been found convenient to add an additional aliquot of the strong protonic acid with the nitrating agent prior to commencement of the second step. The exact amount of additional acid will depend on the acid used, and the nitrating agent, and can be readily determined by the skilled artisan without undue experimentation. For example when concentrated sulfuric acid and concentrated nitric acid is used an additional aliquot of from 10 wt.% to 90 wt.% of concentrated sulfuric acid based on the total weight of the sulfuric/nitric mixture is preferred.

The instant process can be carried out either in batch or continuous phase. However, because of the nature of the reactants, batch processing is preferred. When carrying out the instant process in batch, the time required to activate the pentachlorobenzonitrile in accordance with the two step process will of course vary depending upon the protonic acid used, the concentration and the amount. However, generally, when for example sulfuric acid in the range of 75% concentration is used in molar excess, it has been found that times in the vicinity of from about 15 to 45 minutes at temperatures in the range of 200° to 220° are sufficient to activate the pentachlorobenzonitrile. The time required for nitration can be readily determined since the activated pentachlorobenzonitrile is converted almost quantitatively to the corresponding pentachloronitrobenzene.

The pentachloronitrobenzene is recovered from the crude reaction mixture by conventional means well known in the art. The preferred method involves filtration.

One advantage of the instant process, lies in the fact that the nitrated product is in the form of the mononitrated compound. Thus the chance of handling the more unstable dinitro and trinitro compounds is diminished.

The following examples are given for the purpose of illustration and not by way of limitation.

EXAMPLE I

A clean, dry, 500 cc, 3-necked flask fitted with a reflux condenser, thermometer, and dropping funnel was charged with 10.0 grams (0.036 mole) pentachlorobenzonitrile and 300 cc concentrated sulfuric acid (98 wt.% $H_2SO_4$). The mixture was stirred vigorously at room temperature while a mixture of 20.0 grams concentrated nitric acid and 10 cc concentrated sulfuric acid was added through the funnel in a dropwise manner. The resulting heterogeneous mixture was then heated to a temperature of about 130°C with constant stirring and maintained at this temperature over a period of approximately 6 hours.

Upon cooling the crude reaction mixture was transferred to a separatory funnel partially filled with cracked ice and extracted three times with a 200 cc aliquot of ether. The extracts were combined and washed with an aqueous $NaHCO_3$ solution. This wash was followed by a water washing. The washed extracts were then dried over calcium sulfate and filtered. The ether was then evaporated from the filtrate under reduced pressure to provide 8.0 grams of a pale yellow powder. Infrared spectroscopy showed the spectrum of the analyzed material to be substantially identical to that of a control sample of substantially pure pentachloronitrobenzene.

EXAMPLE II

A clean, dry, 500 cc, 3-necked flask fitted with a reflux condenser, thermometer, and dropping funnel was charged with 10.0 (0.036 mole) pentachlorobenzonitrile and 250 cc concentrated sulfuric acid (98 wt.% $H_2SO_4$). The mixture was heated over a 40 minute period to a maximum temperature of about 220°C and then allowed to cool to room temperature. A 17 cc aliquot of a 50% by volume solution of concentrated nitric acid and 98% sulfuric acid was then added and the contents of the flask heated and maintained at a temperature of 100°C for about 3½ hours.

Upon cooling, the reaction mixture was transferred to a separatory funnel partially filled with cracked ice and extracted three times with 200 cc aliquot of ether. The extracts were combined, dried over magnesium sulfate and filtered. The ether was then evaporated from the filtrate by standard methods to yield a pale yellow solid. Upon drying over-night in a vacuum desiccator, the solid weighed 7.35 g and upon analysis showed the following:

|  | %Cl |
|---|---|
| theoretical | 60.02 |
| actual | 59.9 |

Infrared spectroscopy showed the spectrum of the analyzed material to be substantially identical to that of a control sample of substantially pure pentachloronitrobenzene.

EXAMPLE III

Using the apparatus and procedure of Example II, 10.0 g (0.36 mole) of pentachlorobenzonitrile and 300 cc 98% sulfuric acid was heated over a period of 1¼ hours to a maximum temperature of 217°C. Upon cooling, a 10 cc aliquot of the nitric acid-sulfuric acid solution of Example I was added to the reaction mixture with stirring. The resultant admixture was heated and maintained at 120°C for 5 hours. Upon cooling, the reaction mixture was treated as described in Example I and 8.4 g of a pale yellow solid was isolated. Infrared spectroscopy showed the isolated product to be pentachloronitrobenzene.

While the invention has been explained in relation to its preferred embodiment, it is to be understood that the various modifications hereof will become apparent to those skilled in the art upon reading the specification and is intended to cover such modifications as fall within the scope of the appended claims.

What is claimed is:
1. A process for preparing a pentachloronitrobenzene from the corresponding pentachlorobenzonitrile compound comprising the step of:
   initially heating said pentachlorobenzonitrile compound at temperatures of from about 100°C to about 160°C in the presence of an effective amount of a strong protonic acid and a nitrating agent for a time sufficient to convert said pentachlorobenzonitrile compound to said pentachloronitrobenzene.
2. The process of claim 1 comprising the further step of:
   initially heating said pentachlorobenzonitrile compound with a molar excess of a strong protonic acid at temperatures in excess of 180°C to activate said pentachlorobenzonitrile.
3. The process of claim 2 wherein said strong acid is sulfuric acid having a concentration in excess of 75% $H_2SO_4$ by total weight and said nitrating agent is concentrated nitric acid.
4. A process for preparing a pentachloronitrobenzene from the corresponding pentachlorobenzonitrile comprising the step of:
   heating said pentachlorobenzonitrile in the presence of a molar excess of concentrated sulfuric acid with an effective amount of a nitrating agent selected from the group consisting of concentrated nitric acid and fuming nitric acid at a temperature of from about 130°C to about 160°C for a time sufficient to convert said pentachlorobenzonitrile to said pentachloronitrobenzene.

* * * * *